United States Patent
Lin (10) Patent No.: US 9,301,718 B2
(45) Date of Patent: Apr. 5, 2016

(54) REUSABLE WIRELESS MEDICAL SENSORS

(71) Applicant: Covidien LP, Mansfield, MA (US)

(72) Inventor: Andy S. Lin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 304 days.

(21) Appl. No.: 13/827,303

(22) Filed: Mar. 14, 2013

(65) Prior Publication Data

US 2014/0275884 A1    Sep. 18, 2014

(51) Int. Cl.
| | | |
|---|---|---|
| *H02J 7/00* | (2006.01) | |
| *A61B 5/1455* | (2006.01) | |
| *A61B 5/0205* | (2006.01) | |
| *A61B 5/00* | (2006.01) | |
| *A61L 2/16* | (2006.01) | |
| *A61L 2/24* | (2006.01) | |

(52) U.S. Cl.
CPC ............. *A61B 5/14552* (2013.01); *A61B 5/002* (2013.01); *A61B 5/0205* (2013.01); *A61B 2560/0214* (2013.01); *A61B 2562/24* (2013.01); *A61L 2/16* (2013.01); *A61L 2/24* (2013.01)

(58) Field of Classification Search
CPC ............................... A61L 2/0088; H02J 7/025
USPC ............................................. 320/108; 422/28
See application file for complete search history.

(56) References Cited

U.S. PATENT DOCUMENTS

| | | | | |
|---|---|---|---|---|
| 2007/0074742 A1* | 4/2007 | Lin | ......................... | A61B 19/34 134/18 |
| 2010/0201311 A1* | 8/2010 | Lyell Kirby | ............... | A61L 2/02 320/108 |
| 2012/0326863 A1* | 12/2012 | Johnson | .................. | G09F 3/005 340/539.13 |
| 2013/0294969 A1* | 11/2013 | Chen | ......................... | A61L 2/10 422/28 |
| 2014/0132206 A1* | 5/2014 | Zhu | ................................ | 320/108 |

FOREIGN PATENT DOCUMENTS

WO        2007015833 A2       2/2007

OTHER PUBLICATIONS

U.S. Appl. No. 13/462,253, filed May 2, 2012, Bo Chen et al.
U.S. Appl. No. 13/462,291, filed May 2, 2012, Bo Chen et al.
U.S. Appl. No. 13/462,328, filed May 2, 2012, Bo Chen et al.

* cited by examiner

*Primary Examiner* — Edward Tso
*Assistant Examiner* — Johali Torres Ruiz
(74) *Attorney, Agent, or Firm* — Fletcher Yoder PC (57) ABSTRACT

Embodiments of the present disclosure relate to reusable wireless sensors. According to certain embodiments, the wireless sensor may include a rechargeable battery coupled to an induction coil for recharging the battery. One or more magnets may be disposed within or coupled to the wireless sensor, and the one or more magnets may be arranged to align the induction coil of the wireless sensor with a recharging device to facilitate recharging the battery of the wireless sensor.

22 Claims, 7 Drawing Sheets

REUSABLE WIRELESS MEDICAL SENSORS

BACKGROUND

The present disclosure relates generally to medical devices and, more particularly, to wireless medical sensors such as those used for pulse oximetry.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices has been developed for monitoring many such physiological characteristics. These devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time-varying amount of arterial blood in the tissue during each cardiac cycle.

Pulse oximeters and other types of monitoring devices may use either disposable sensors, which are discarded after a single use, or reusable sensors. Reusable sensors may lower the overall cost of sensor per use; however, reusable sensors must be thoroughly disinfected after each use.

Additionally pulse oximetry sensors may communicate with a patient monitor using a communication cable. For example, a sensor may use such a communication cable to send a signal corresponding to a measurement performed by the sensor to the patient monitor for processing. However, the use of communication cables may limit the applications available, as the cables may limit a patient's range of motion by physically tethering the patient to a monitoring device.

Although wireless sensors may transmit information without the need for a communication cable, the sensors typically rely on batteries to power the sensor. As batteries afford a limited power source, wireless sensors may be operational only for a limited amount of time before the battery is depleted and must be recharged or replaced to continue sensor operation. Generally, a battery-powered sensor utilizes a removable battery, which results in a sensor housing with crevices or openings that may increase the difficulty of disinfecting the sensor. Some battery-powered sensors that utilize rechargeable batteries need to be plugged into a power source via an electrical connector, thus such sensors have openings or portions to receive the charging cable that similarly increase the difficulty of disinfecting the sensor.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In certain circumstances, it may be desirable for a reusable sensor to have a structure that facilitates efficient and thorough disinfecting. For example, it may be desirable for a reusable, wireless pulse oximetry sensor to have a rechargeable battery that is encapsulated by or sealed within a housing in order to minimize or eliminate the number of crevices in the housing and/or electrical connectors. Encapsulating the rechargeable battery within the sensor house and eliminating crevices or openings in the sensor housing may allow for efficient and effective disinfecting of the sensor. Furthermore, the battery of such a reusable wireless sensor will need to be periodically recharged. Accordingly, it may be desirable to have a reusable wireless sensor that is configured to be easily disinfected and that has a rechargeable battery that is easily recharged.

With the foregoing in mind, some wireless sensors, such as those used for pulse oximetry, generally lack an encapsulating housing to facilitate disinfecting and do not have a configuration that facilitates battery recharging. Moreover, some systems for recharging batteries of wireless sensors require plugging the sensor into a wired connector, manually securing the sensor to a recharging device, or otherwise manipulating the sensor to effect recharging of the battery. To address these issues, the present embodiments describe a wireless sensor that is equipped with a rechargeable battery and an induction charging coil to enable recharging of the sensor without having to plug the sensor into a wired connector. Furthermore, the present embodiments describe a wireless sensor that is equipped with one or more magnets (e.g., ferromagnetic materials) to easily, and in some cases automatically, align the sensor with one or more corresponding magnets of a charging device. Thus, the described systems may eliminate the need to manually align or attach the sensor to the charging device, as well as reduce instances of inaccurate alignment of the sensor and the charging device. The magnets may also assist in holding the sensor in proximity (e.g., over, adjacent, etc.) to the charging device for the duration of the recharging process. Embodiments such as these are discussed with respect to FIGS. 1, 2, 7, and 8.

As reusable sensors are disinfected after each use, it may be desirable to recharge the sensor while disinfecting to minimize the time that the sensor is unavailable for use. Thus, the present embodiments describe a system configured to concurrently charge and disinfect one or more sensors. Furthermore, because the described system charges a rechargeable battery of the sensor via induction, the circuitry and the rechargeable battery of the sensor may be fully sealed and enclosed within the sensor housing, without the need for openings to remove the battery or to connect the sensor to a power source via a wired connection. Thus, the fully sealed and enclosed sensor may be submerged in a variety of disinfecting agents, including disinfecting solutions, without damaging the internal electrical components sealed within the sensor. Furthermore, the described charging system may include one or more magnets to attract and/or align with the magnets of the sensor, thus aligning the sensor with the charging device. Embodiments of such charging and disinfecting systems are discussed below with respect to FIGS. 3-7, 9, and 10. These charging and disinfecting systems may be used alone or in any combination as discussed with respect to FIGS. 1, 2, 7, and 8.

Additionally, the present embodiments describe a sensor having an indicator, such as a dye, disposed (e.g., embedded, impregnated, etc.) within the sensor. When the housing of the sensor is damaged (e.g., punctured, deteriorated, etc.), the dye may exit (e.g., leach, move, seep, etc.) out of the housing. In some cases, the dye may leach out of the housing when the damaged sensor is placed in solution, such as a disinfecting solution. Thus, the presence of the dye in the disinfecting solution may help a user identify whether the housing is broken or punctured and whether the sensor should be discarded or repaired. In addition, the absence of the dye in the disinfection solution may confirm or help a user positively determine that the sensor is structurally intact and in condition for use. Embodiments such as these are discussed below with respect to FIGS. 11-14. Such indicators may be used alone or in any combination with the sensors and charging and disinfecting systems discussed in detail with respect to FIGS. 1-10.

Figure 1:
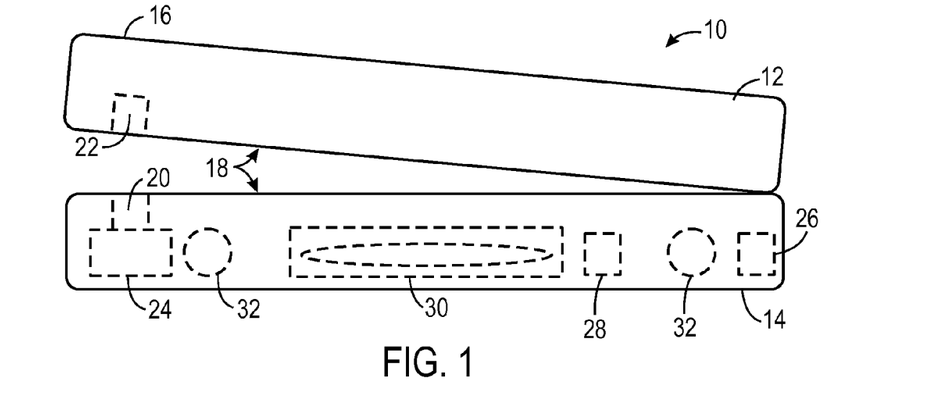
FIG. 1 is a side view of a pulse oximetry sensor, in accordance with an embodiment.
Figure 2:
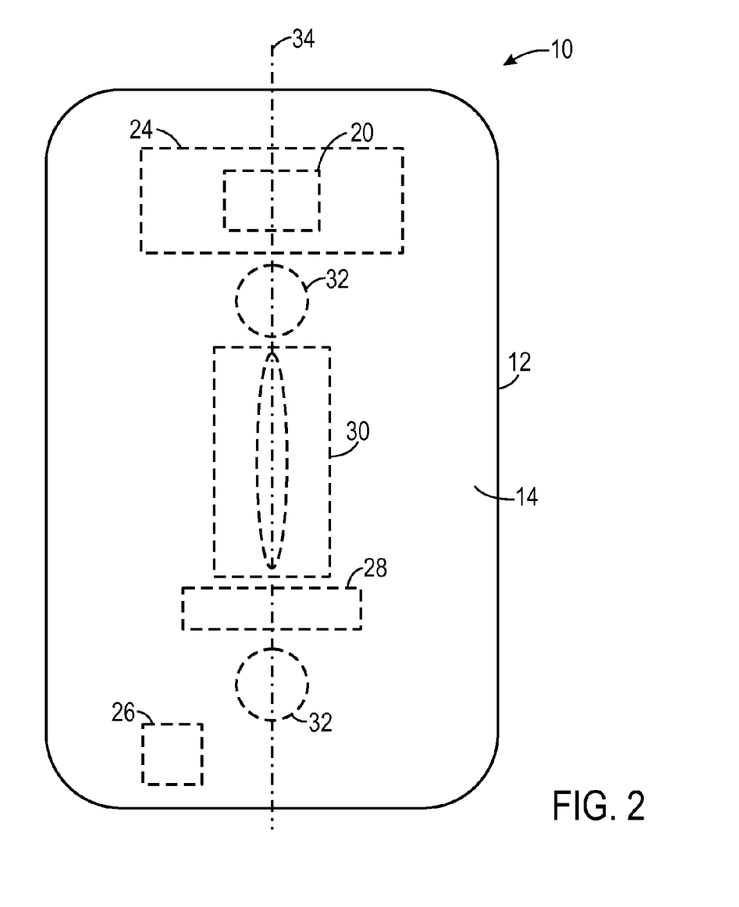
FIG. 2 is a bottom view of the pulse oximetry sensor of FIG. 1, in accordance with an embodiment.

With the foregoing in mind, FIGS. 1 and 2 illustrate side and bottom views, respectively, of an embodiment of a wireless sensor 10 in accordance with the present disclosure. The depicted sensor is a clip-style sensor that may be clipped onto a target tissue, such as clipped to a patient's fingertip, toe, or earlobe, for example. The sensor 10 may include a housing 12, which is adapted to fit about or clip to the tissue of the patient. In such clip-style sensors, the sensor 10 may have a bottom portion 14, a top portion 16, and two patient or tissue contacting surfaces 18, as shown in FIG. 1.

While FIG. 1 depicts a clip-style sensor 10, various styles of reusable pulse oximetry sensors are contemplated. For example, the sensor may be adapted to fit on a variety of pulsatile tissue regions of the patient. In some embodiments, the sensor 10 may be adapted to be disposed on a forehead of the patient, for example. Thus, in some embodiments, the sensor may have a single portion adapted to fit to the patient's forehead (as opposed to the clip-style having the bottom portion 14 and top portion 16). Furthermore, while the sensor 10 is presented as a pulse oximetry sensor by way of example, it should be understood that other types of sensors may similarly benefit from the techniques discussed herein.

When sensor 10 is configured for pulse oximetry techniques, the sensor 10 may be placed on the patient in a location that is normally perfused with arterial blood to facilitate measurement of desired physiological parameters, such as arterial oxygen saturation measurement ($SpO_2$). To acquire a signal corresponding to one or more physiological parameters of the patient, the sensor 10 may include one or more emitters 20 and one or more detectors 22. The emitter 20 and de/tector 22 may be disposed in the housing 12 and are electrically coupled to circuitry 24. The emitter 20 and detector 22 may be configured to operate in various modes (e.g., reflectance or transmission). For example, the emitter 20 may be disposed in either the bottom portion 14 or the top portion 16. The detector 22 may be disposed in either the bottom portion 14 or the top portion 16, in either the same or different portion 14, 16 (e.g., the opposite portion) as the emitter 20. For pulse oximetry applications, the emitter 20 may have two LEDs, where each LED is configured to transmit light at certain wavelengths (e.g., RED light and/or IR light) into the tissue, wherein the RED light may have a wavelength of about 600 nm to about 700 nm, and the IR light may have a wavelength of about 800 nm to about 1000 nm. The detector 22 may receive the RED and IR light after it has passed through or is reflected by the tissue and convert it into an electrical signal. The amount of light that passes through the patient tissue and other characteristics of light waves may vary according to the changing amount of certain blood constituents in the tissue and the related light absorption and/or scattering. The circuitry 24 may include an analog-to-digital converter for digitizing the electrical signal received from the detector 22. As should be appreciated, however, the circuitry 24 within the sensor housing 12 may also include additional components for further signal processing or calculating a physiological parameter from the signal.

In certain embodiments, the sensor 10 is configured to communicate wirelessly. For example, the sensor 10 may have a radio-frequency (RF) transceiver 26. The RF transceiver 26 may transmit a raw digitized detector signal, a processed digitized detector signal, and/or a calculated physiological parameter, as well as any data that may be stored in the sensor, as discussed below. For example, in certain embodiments, the circuitry 24 may include a signal processing component configured to calculate one or more parameters of interest (e.g., oxygen saturation) to reduce the amount of information transmitted by the RF transceiver 26. That is, the RF transceiver 26 may only transmit one or more parameters received from a signal processing component rather than the raw or processed digitized detector signal. The RF transceiver 26 may establish wireless communication with a wireless receiver (e.g., a patient monitor, a multi-parameter patient monitor, or a wireless access point) using any suitable protocol.

In the illustrated embodiment, the RF transceiver 26 wirelessly transmits data by digital radio signals. However, in certain embodiments, the sensor 10 may include any number of wireless modules, which may be capable of communications using the IEEE 802.15.4 standard, and may be, for example, ZigBee, WirelessHART, or MiWi modules. Additionally or alternatively, the wireless module may be capable of communicating using the Bluetooth standard, one or more of the IEEE 802.11 standards, an ultra-wideband (UWB) standard, or a near-field communication (NFC) standard. In the illustrated embodiment, the wireless module may be the RF transceiver 26 that may be capable of longer range transmission and may be capable of communicating with a radio-frequency identification (RFID) tag of a patient.

In some embodiments, the sensor 10 may also include a security device. Pulse oximetry sensors 10 are generally relatively small devices that patients may inadvertently remove or carry out of the hospital or clinic, for example. Thus, the sensor may incorporate a radio frequency identification (RFID) tag that triggers an alarm when the sensor passes through a check point near an entrance of the hospital or clinic, for example.

The RF transceiver 26 may provide other advantages as it allows the sensor 10 to communicate with a monitor and other devices without a cable. Thus, the wireless sensor 10 depicted in FIG. 1 does not require physical connection to a communication cable and does not have crevices, ports, sockets, or openings for receiving the communication cable, for example. As discussed above, such crevices and openings in the sensor housing 12 may make the sensor 10 more difficult to clean and disinfect, and thus less suitable for reuse. In accordance with some embodiments of the present disclosure, a wireless sensor 10 may be configured to have no crevices or openings, in order to allow for easy cleaning and disinfecting.

To facilitate disinfecting of the sensor 10, the housing 12 may be formed from any suitable material that can be disinfected and can be shaped to minimize or eliminate crevices. Additionally, the housing 12 may be formed from a material that may protect the internal components (e.g., emitters 20, detectors 22, circuitry 24, wireless transceiver 26, battery 28, etc.) of the sensor 10 from a variety of disinfecting agents (e.g., disinfecting solution, disinfecting gas, or UV light). In particular, the housing 12 may be resistant to or may prevent fluid infiltration. For example, the housing 12 may be formed from rigid or conformable materials, such as rubber or elastomeric compositions (including acrylic elastomers, polyimide, silicones, silicone rubber, celluloid, PMDS elastomer, polyurethane, polypropylene, acrylics, nitrile, PVC films, acetates, and latex). Further, the sensor 10 may be formed from molded or overmolded components.

Additionally, it may be desirable for the housing 12 to encapsulate the internal components of the sensor 10 such that no internal components are designed to be removable or connected to an electrical connector. For example, wireless sensors 10 generally include a battery to power the sensor 10, however batteries typically must be recharged or replaced as the battery depletes with use. Removing a battery to replace or recharge the battery may require an opening or a door in the housing 12. Alternatively, recharging a battery without removing it typically requires an electrical connector. Either design may result in several crevices or openings in the housing 12 that are difficult to disinfect. In an embodiment, the housing 12 of the sensor 10 continuously or fully encapsulates the electrical components of the sensor 10, such that the electrical components are not exposed to the external environment. In an embodiment, the housing 12 forms an integral shell or case surrounding the electrical components. The electrical components are not intended to be removed, and are not removable without breaking or damaging the housing 12. Thus, the housing 12 seals the electrical components, enabling the sensor 10 to be submerged in a liquid solution, such as for example, the disinfecting solution, without exposing the electrical components to the liquid solution.

Thus, in certain embodiments of the present disclosure, the sensor 10 may include a rechargeable battery 28 electrically connected to an induction coil 30. The battery 28, for example, may be a lithium ion, lithium polymer, nickel-metal hydride, or nickel-cadmium battery. The induction coil 30 may facilitate recharging of the battery 28, thus allowing for the battery 28 to be sealed within the housing 12 without requiring removal of the battery 28 for recharging or connecting the battery 28 to a charging device via a wired connection. In some embodiments, the induction coil 30 may include electrically conductive wire configured to receive energy from an electromagnetic field and to convert the energy into electric current, which may be used to charge the battery 28.

Furthermore, in certain embodiments, the sensor 10 may include or may be coupled to one or more magnets 32 (e.g., ferromagnetic materials, such as iron, nickel, cobalt and their alloys) that are configured to align with one or more magnets in the external charging device, as described in more detail below. The one or more magnets 32 may be disposed within the sensor housing 12, although in some embodiments the one or more magnets 32 may be disposed on a surface of the housing 12 or may be otherwise coupled to the sensor 10. The one or more magnets 32 may be disposed within or coupled to any portion of the sensor 10, including the bottom portion 14 and/or the top portion 16. In certain embodiments, it may desirable to include or couple the magnets 32 to the portion of the sensor 10 that includes the battery 28, for example, the bottom portion 14 of the sensor 10. In such cases, the bottom portion 14 of the sensor 10 may be heavier than the top portion 16, thus pulling or "flipping" the sensor 10 to orient and align the bottom portion 14 of the sensor 10 with the charging station when the sensor 10 is placed in the charging device, for example. In other words, such sensors 10 may be configured to automatically achieve a suitable orientation, wherein the bottom portion 14 is positioned below (e.g., under) the top portion 16 to facilitate recharging of the battery. For example, the sensor 10 may automatically orient itself to position the bottom portion 14 below the top portion 16 as the sensor 10 sinks in a volume of a solution when the sensor is placed in the solution.

In the embodiment depicted in FIGS. 1 and 2, two magnets 32 are positioned on opposing sides of the induction coil 30 and along a longitudinal axis 34 of the bottom portion 14 the sensor 10. However, in other embodiments, three, four, five, or more magnets 32 may be coupled to or disposed within the sensor 10 in various configurations to facilitate alignment of the sensor 10 with the external charging station. For example, three or more magnets 32 may be arranged circumferentially around the induction coil 30, so as to form a ring around the induction coil 30. In some embodiments, one magnet 32 having an annular or ring shape may surround or substantially surround the induction coil 30. Additionally, each magnet 32 may take any shape or form, such as, for example, a curved shape, a circular shape, or a rectangular shape. The one or more magnets 32 generally have a suitable configuration and a suitable strength to facilitate the alignment of the sensor 10 with the charging station, to bring the battery 28 into alignment and proximity with the charging station.

Figure 3:
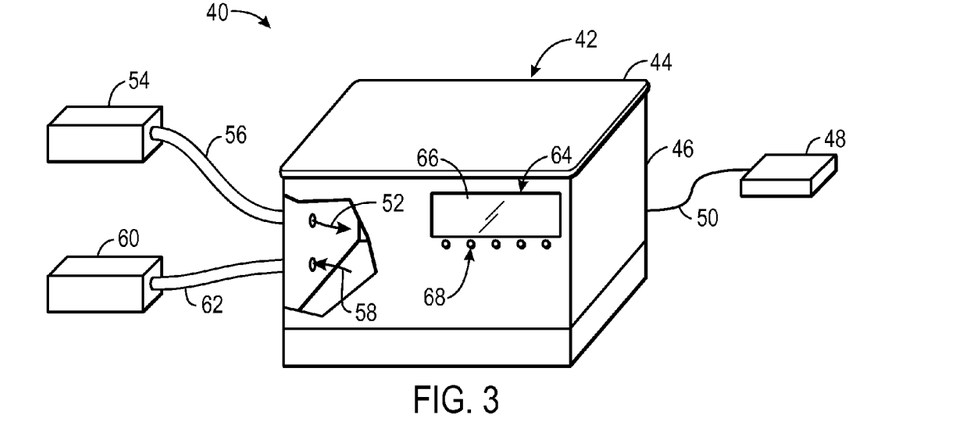
FIG. 3 is a perspective view of a system, including a charging and disinfecting device for charging and disinfecting the sensor, in accordance with an embodiment.

Turning to FIG. 3, a perspective view of a charging and disinfecting system 40 for charging and disinfecting the sensor 10 is illustrated. It should also be appreciated that the charging and disinfecting system 40 may also be utilized for charging and disinfecting a variety of other types of sensors and medical devices equipped with an induction coil and/or one or more magnets. As depicted, the system 40 includes a charging and disinfecting device 42. The device 42 may include a lid 44 and/or a housing 46, in certain embodiments. The lid 44 and the housing 46 may be constructed from any number, and any combination, of suitable materials, such as plastics, metals, or glasses. Additionally, the device 42 may include a power supply or may be connected to an external power supply 48 by a wired connection 50.

In some embodiments, the device 42 may be configured to be used with one or more disinfecting agents (e.g., a disinfecting solution or gas). Various disinfecting agents may be suitable for disinfecting medical devices. The device 42 may include one or more inlets 52 for receiving the disinfecting agent. The inlets 52 may be positioned at various locations on the device 42. As shown in FIG. 3, the inlet 52 is positioned in a wall of the housing 46 and the disinfecting agent is supplied by a supply unit 54 through an inlet tubing 56 into the housing 46 of the device 42. Alternative methods of supplying the disinfecting agent are also envisioned. For example, an operator may pour the disinfecting agent through a top opening into the housing 46 before closing the lid 44. Additionally, in some embodiments, the device 42 may include an outlet 58 through which the disinfecting agent is removed from the device 42 after the sensor 10 is disinfected. In such embodiments, the disinfecting agent to be removed may be passed to a waste disposal unit 60 through outlet tubing 62. The device 42 may also include a control circuit 64, display 66, and one or more inputs 68. The control circuit 64 may be configured to carry out and control various processes related to charging and disinfecting the sensor 10, as described in more detail below.

Figure 4:
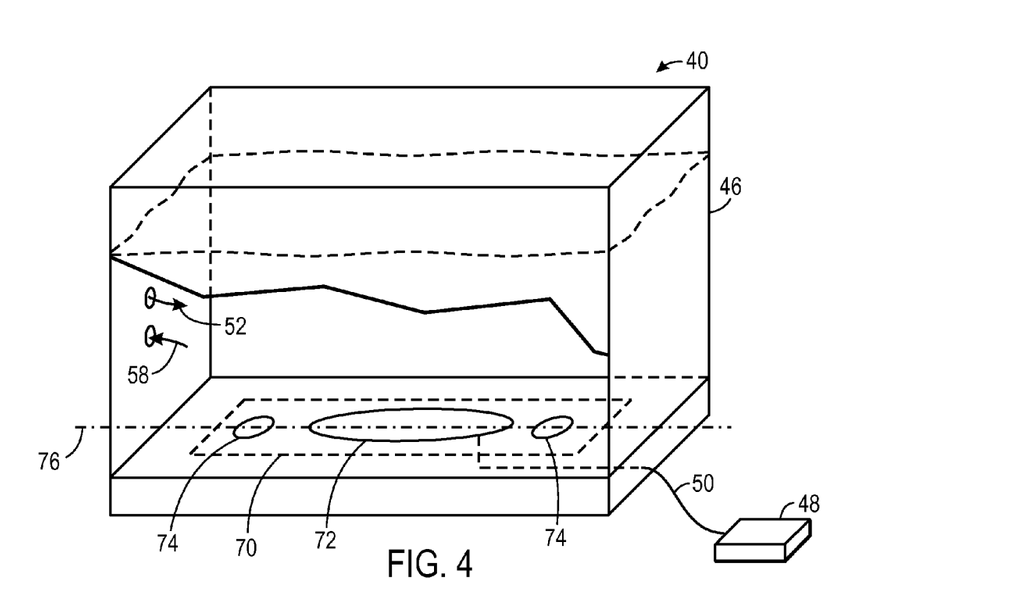
FIG. 4 is a perspective view of the charging and disinfecting device of FIG. 3, including a charging station, in accordance with an embodiment.

FIG. 4 depicts internal components of an embodiment of the charging and disinfecting device 42. As shown, the device 42 may include one or more charging stations 70. The charging station 70 may include an induction coil 72 and one or more magnets 74. In certain embodiments, the induction coil 72 and the one or more magnets 74 may be configured to align with (e.g., correspond to) the induction coil 30 and the one or more magnets 32 of the sensor 10. For example, the induction coil 72 may be of a substantially similar size (or larger) as the induction coil 30 of the sensor 10 (or the general type of sensor 10) that the charging station 70 is configured to recharge. Additionally, the one or more magnets 74 in the charging station 70 may be arranged in a substantially similar pattern or configuration as those magnets 32 of the sensor 10, or may be arranged so as to generally attract and/or align the sensor 10 in a way suitable for charging the battery of the sensor 10 via induction. Thus, it should be appreciated that a variety of geometries for the induction coil 72 and the one or more magnets 74 may be suitable, including the arrangements described above with respect to the induction coil 30 and magnets 32 of the sensor 10. For example, two magnets 74 may be positioned around the outer circumference of the induction coil 72 and along an axis 76 of the device 42. In some embodiments, the charging station 70 may be designed for aligning with and charging a specific type of sensor 10. For example, the charging station 70 and/or the various components therein may be larger for adult sensors compared with a charging station 70 configured for use with pediatric sensors. In some embodiments, the charging station 70 may have more magnets 74 and/or stronger magnets 74 for use with adult sensors compared to charging stations 70 for use with pediatric sensors.

The charging station 70 within the device 42 may also have features to assist an operator in visualizing the charging station 70 and determining whether the sensor 10 is adequately (e.g., properly) aligned with the charging station 70. For example, the charging station 70 may be colored, surrounded by a line, or otherwise marked so as to provide a visual indication when the sensor 10 is properly aligned with the charging station 70. For example, an operator may be able to observe whether a sensor 10 is generally positioned within a lined box or other visual indicator surrounding the charging station 70 area, and if so, then the operator may be able to determine that the sensor 10 is properly aligned with the charging station 70.

The main power supply 48 may also supply power to the induction coil 72 of the charging station 70, as shown in FIG. 4. The induction coil 72 may include a plurality of windings of electrically conductive wire to receive electrical power from the main power supply 48. When coupled to the main power supply 48, the induction coil 72 creates an electromagnetic field which may induce an electrical current in the induction coil 30 of the sensor 10 when the two induction coils 30, 72 are brought within proximity of each other. In particular, the configuration of the charging station 70 (e.g., the position of the induction coil 72 and the one or more magnets 74) may allow the induction coil 30 of the sensor 10 and the induction coil 72 of the charging station 70 to be in operational proximity, and the induction coil 72 of the charging station 70 may induce an electrical current in the induction coil 30 of the sensor 10. The one or more magnets 74 of the charging station 70 and the one or more magnets 32 of the sensor 10 may automatically align the sensor 10 with the charging station 70, as described above. In some embodiments the magnets 74 and the magnets 32 may further hold the sensor 10 in place during the charging and/or disinfecting session. In certain embodiments, the device 42 may include a method of disinfectant agitation to promote flow and/or distribution of a disinfecting agent around the sensor 10 (e.g., a rotor or a fan disposed in the device 42). Thus, in some embodiments, the one or more magnets 74 may be of sufficient strength to hold the sensor 10 in place over the charging station 70 while the disinfecting solution is agitated or swirled around the sensor 10.

Figure 5:
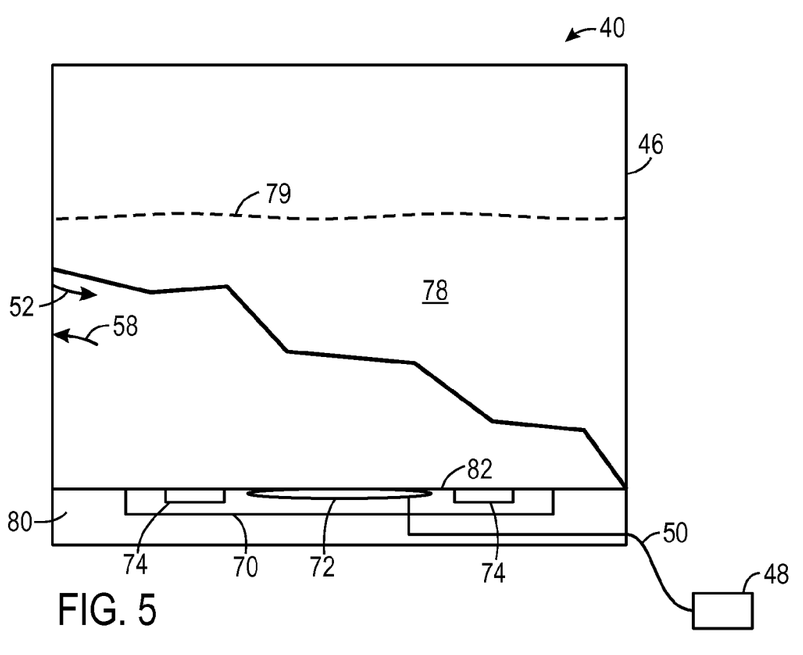
FIG. 5 is a side view of the charging and disinfecting device of FIG. 3, in accordance with an embodiment.

FIG. 5 illustrates a side view of the charging and disinfecting device 42. A portion of the device 42 is cut away to show certain internal components of a bottom portion 80 of the device 42. As depicted, the housing 46 may be configured to receive and to hold a disinfecting agent 79 within a disinfecting chamber 78. In certain embodiments, the charging station 70 may be disposed within or integrated into the bottom portion 80, which may be generally below or outside of the disinfecting chamber 78 (e.g., below or outside of a bottom surface 82 of the disinfecting chamber 78). In certain embodiments, as shown, the bottom surface 82 may be generally horizontal. Thus, the induction coil 30 of the sensor 10 may receive electrical power from the induction coil 72 of the charging station 70, which is disposed in the bottom portion 80, when the induction coil 30 of the sensor 10 is brought into alignment with the bottom surface 82. As discussed herein, the magnets 32 may align the induction coil 30 of the sensor 10 with the bottom surface 82 of the disinfecting chamber 78. Configurations of the device 42 having the bottom portion 80 may facilitate easy removal, replacement, and/or repair of the charging stations 70, as an operator may be able to access the charging stations 70 more easily if disposed in the bottom portion 80 below, or outside of, the disinfecting chamber 78. Additionally, such a configuration may protect the components (e.g., induction coil, magnets, etc.) from the disinfecting agent 79.

In certain embodiments, rather than being integrated into the bottom portion 80 below the bottom surface 82, the charging station 70 may be coupled to or disposed on (e.g., mounted on) the bottom surface 82 of the disinfecting chamber 78. As noted above, the bottom surface 82 may be generally horizontal, and thus, the charging station 70 and/or the induction coil 72 of the charging station 70 may have a generally horizontal orientation. When a sensor 10 is placed (e.g., dropped, deposited, etc.) into the device 42, the sensor 10 may drop or sink towards the charging station 70. The magnets 32 of the sensor 10 may align the induction coil 30 with the bottom surface 82 (e.g., the magnets 32 may align the induction coil 30 in a generally horizontal orientation, parallel to the bottom surface 82 and/or parallel to the induction coil 72 of the charging station 70) to enable the induction coil 30 to receive electrical power from the induction coil 72 of the charging station 70. Regardless of the particular placement of the charging station 70, the charging station 70 may provide or be disposed under a substantially or generally horizontal or flat surface or platform, which may facilitate aligning the sensor 10 with the charging station 70 and may enable the induction coil 30 of the sensor 10 to receive electrical power from the induction coil 72 of the charging station 70.

Figure 6:
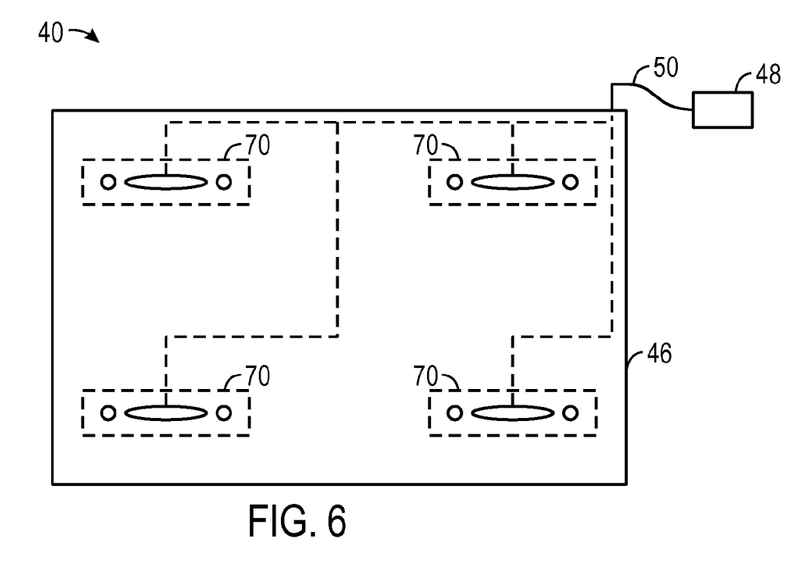
FIG. 6 is a top view of the charging and disinfecting device, including a plurality of charging stations, in accordance with an embodiment.

FIG. 6 depicts a top view of one embodiment of the device 42 having a plurality of charging stations 70. As shown, the charging stations 70 may be arranged at various locations within the device 42. In the illustrated embodiment, four separate charging stations 70 are generally positioned in the four corners of the device 42. However, two, three, five, six, seven, or more charging stations 70 may be included in the device 42. Furthermore, the plurality of charging stations 70 may be arranged in any manner that allows for one or more sensors 10 to be aligned with the charging stations 70. A suitable amount of space between the charging stations 70 may be required so that the magnets 32 of the sensor 10 are not drawn to the respective magnets 74 of two adjacent charging stations 70. For example, the respective magnets 74 of two charging stations 70 may be separated by a distance greater than the distance between the magnets 32 of the sensor 10 so that the sensor 10 is not inadvertently attracted to or spread across two different charging stations 70. As depicted, each charging station 70 may be connected to the power supply 48 via wired connections 50.

Figure 7:
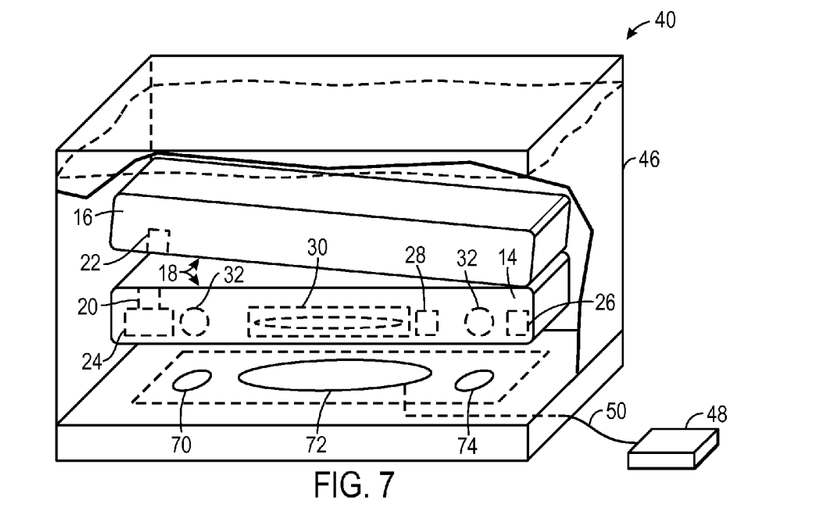
FIG. 7 is a side view of the charging and disinfecting device, having the sensor of FIG. 1 disposed therein, in accordance with an embodiment.

As illustrated in FIG. 7, the sensor 10 may be placed (e.g., dropped, deposited, etc.) within the charging and disinfecting device 42, and the sensor 10 may align with the charging station 70 for recharging the battery 28. As discussed above, the magnets 32 of the sensor 10 may be disposed in the bottom portion 14 of the sensor 10. Thus, the bottom portion 14 of the sensor 10 may be heavier than the top portion 16 of the sensor 10. Such a weight distribution may turn or flip the sensor 10, so that the bottom portion 14 is below the top portion 16, enabling the bottom portion 10 to align with the charging station 70. Alignment of the sensor 10 and the charging station 70 is also facilitated by magnets 74. In particular, the charging station 70 may include magnets 74 having a size and/or shape that corresponds to the magnets 32 of the sensor 10. Generally, the magnets 74 may attract the magnets 32 of the sensor 10, automatically aligning the sensor 10 with the charging station 70. In the depicted embodiment, two magnets 32 in the sensor 10 are aligned with two magnets 74 in the charging station 70, although any of number of magnets 32, 74 may be suitable, as discussed above. Furthermore, the size and shape of the magnets 74, 32 do not necessarily need to be identical, as long as the magnets 74 of the charging station 70 and magnets 32 of the sensor 10 are configured to align the sensor 10 with the charging station 70. Moreover, the charging station 70 is configured such that the induction coil 72 aligns with and is brought into operational proximity of the induction coil 30 of the sensor 10 when the magnets 32 of the sensor 10 and the magnets 74 of the charging station 70 are drawn towards each other.

The sensor 10 may be configured to align with the charging station 70 if a solution is present in the device 42 or if no solution is present in the device 42. More particularly, in some embodiments, the device 42 may be filled with a disinfecting agent (e.g., a disinfecting solution) before the sensor 10 is placed in the device 42. In such cases, the weight of the sensor 10 may cause the sensor 10 to be submerged in the disinfecting agent and to sink towards the charging station 70 located at the bottom of the device 42. Additionally or alternatively, the pull of the magnets 32, 74 or attraction between the magnets 32, 74 may draw the sensor 10 towards the charging station 70 located at or within the bottom portion 80 of the device 42. Furthermore, as discussed above, the sensor 10 may be configured to automatically orient the sensor 10 for recharging by flipping or turning so that the bottom portion 14 (or any portion having the battery 28, induction coil 30, and magnet 32) is directed towards the bottom portion 80 of the device 42. The magnets 32 in the sensor 10 and the magnets 74 in the charging station 70 may then align the sensor 10 with the charging station 70. Once the sensor 10 is properly aligned with the charging station 70, the charging station 70 may supply a charge to the induction coil 30 of the sensor 10 via induction. Furthermore, the device 42 may have a structure that can detect the presence of the sensor 10 (e.g., a motion sensor, a weight sensor, or the like), and when the sensor 10 is detected in the device 42, a timer for the disinfecting time may automatically begin. For example, a typical clip-style sensor 10 may need to be disinfected for a certain minimum length of time. Thus, when the device 42 detects that the sensor 10 has been dropped into the disinfecting solution of the device 42, the timer may automatically begin. Upon completion of the time, an alert or indicator may be provided via the device 42 and/or the disinfecting solution may be drained.

As mentioned above, in other embodiments, the sensor 10 may be placed in and/or charged in the device 42 even if no disinfecting agent is present in the device 42. In such embodiments, once the sensor 10 is placed into the device 42, the magnets 32 in the sensor 10 and the magnets 74 in the charging station 70 may align the sensor 10 with the charging station 70. Once aligned properly, an indication that the induction coil 30 of the sensor 10 is properly aligned may be provided to an operator via an indicator or via the display 66. Upon receiving the indication that the induction coil 30 of the sensor 10 is properly aligned, the operator may dispense the disinfecting agent into the device 42, or the operator may provide an input instructing the system 40 to charge the sensor 10 and/or provide the disinfecting agent. Alternatively, once the induction coil 30 of the sensor 10 is determined to be properly aligned with the charging station 70, the system 40 may be configured to automatically charge the sensor 10 and/or to automatically dispense the disinfecting agent into the device 42. The magnets 32 and the magnets 74 may be of a suitable strength to hold the sensor 10 in place in proximity (e.g., over, adjacent, etc.) to the charging station 70 while the disinfecting agent is dispensed into the device 42. Alternatively, the sensor 10 may be charged at the charging station 70 without disinfecting.

Figure 8:
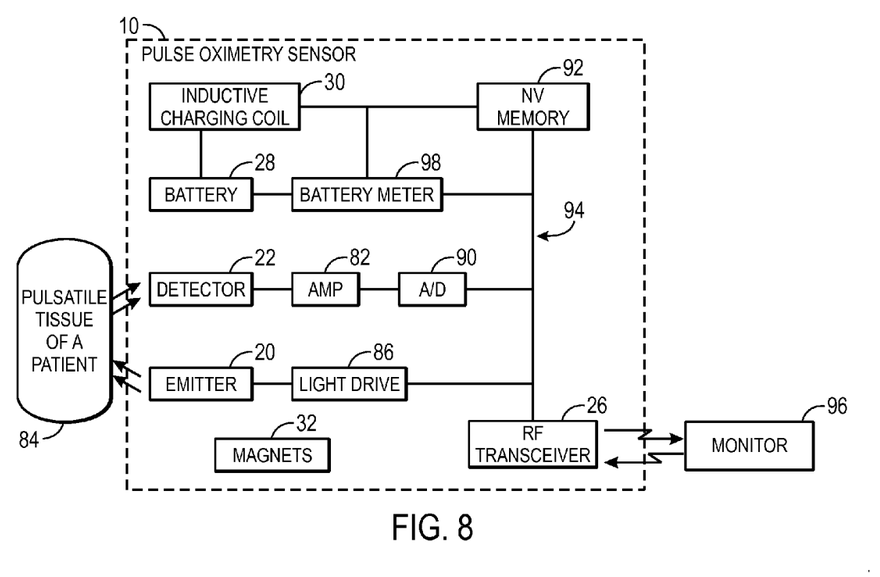
FIG. 8 is a block diagram of the components of an example of the pulse oximetry sensor of FIG. 1, in accordance with an embodiment.

In accordance with one embodiment, FIG. 8 illustrates a plurality of components that may be present within the housing 12 of the sensor 10 to facilitate the acquisition, processing, and transmission of the physiological parameter data from a patient 84. The sensor 10 may also include a light drive 86 configured to drive the emitter 20 based on the control signals to emit light into a pulsatile tissue of the patient 84. The detector 22 may detect the light after it has passed through the tissue of the patient 84. The received signal from the detector 22 may be passed through an amplifier 88 and an analog-to-digital (A/D) converter 90 for amplifying and digitizing the electrical signals from the sensor 10. The digital data may then be stored in a non-volatile (NV) memory 92, which may be coupled to the main system bus 94. Additionally, the NV memory 92 may also store historical data and/or values (e.g., detector signal data, data points, trend information) for the physiological parameter of the patient. For example, the NV memory 92 may store information regarding the wavelength of one or more light sources of the emitter 20, which may be sent to a patient monitor 96 to allow for selection of appropriate calibration coefficients for calculating a physiological parameter (e.g., blood oxygen saturation). The RF transceiver 26 may also receive control signals from the monitor 96. In the illustrated embodiment, the signal processing may be somewhat minimal to reduce the number of internal components of the sensor 10 and reduce bulkiness. However, certain embodiments may include additional or more complex signal processing or may calculate a physiological parameter from the detector signal data.

Additionally, the sensor 10 and the charging device 42 may be in communication (e.g., wireless communication), such that the sensor 10 may relay information to the charging device 42, and vice versa. For example, in certain embodiments, the sensor 10 may include a battery meter 98 to provide the expected remaining power of the battery 28 to the device 42. In some embodiments, the sensor 10 may provide an indication that the sensor 10 is properly aligned with the charging station 70, and/or the sensor 10 may provide an indication that charging is complete. The information may, in turn, be provided to a user via the display 66 on the device 42. In embodiments where the charging device 42 includes a plurality of charging stations 70 (discussed further below), the display 66 may provide information that the sensor 10 is aligned with a particular charging station 70 by identifying the aligned charging station 70 by number or other identifying information. For example, the display 66 may provide information that the sensor 10 is aligned with a first charging station. Alternatively or additionally, the charging station 70 may provide a user-perceivable indication. For example, the charging station 70 may be lit when aligned with a sensor, such as having a green indicator when the sensor 10 is properly aligned with the charging station 70. In some embodiments, charging stations 70 that are not aligned with any sensors 10 (i.e., charging stations 70 that are not in use) may have no indicator or may have a red indicator to indicate that the charging station 70 is not aligned with any sensor 10. Thus, the operator may be able to determine the number of charging stations 70 available.

Figure 9:
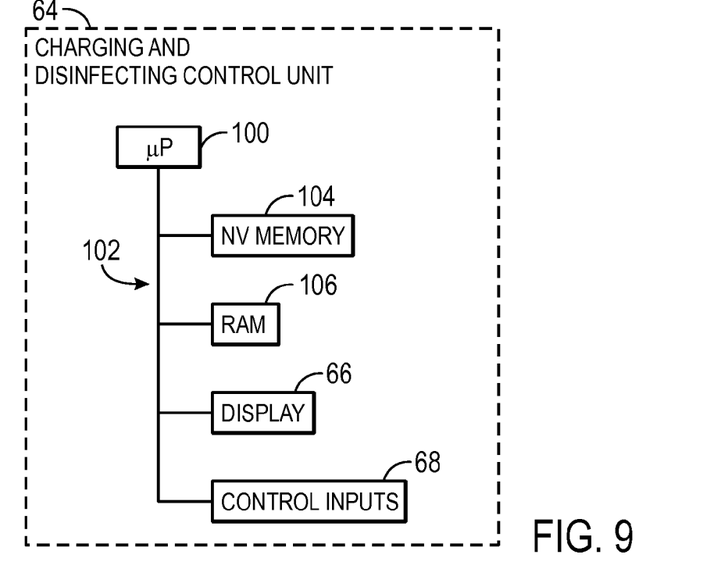
FIG. 9 is a block diagram of the components of an example of the control circuit of the charging and disinfecting device of FIG. 3, in accordance with an embodiment.

To facilitate the processing and display of the data downloaded from the sensor 10, the device 42 may include the control circuit 64, which may include a plurality of components as illustrated by FIG. 9, in accordance with an embodiment.

For example, the control circuit 64 may include a microprocessor 100 which may be coupled to a main system bus 102, which is also coupled to a NV memory 104, a RAM 106, the display 66, and the control inputs 68. The display 66 may provide information to a user regarding the status of the sensor 10 (e.g., battery meter, number of recharges, or number of disinfecting cycles). Further, the display 66 may provide a recommendation to replace one or more sensors 10. For example, the control circuit may determine that a sensor 10 should be replaced based at least in part upon the received information regarding the status of the sensor 10 (e.g., whether recharging is complete, whether disinfecting is complete, whether the housing is damaged as discussed below, etc.). Additionally, the display 66 may also provide information regarding the disinfecting and charging cycle (e.g., disinfection agent selected, percent of cycle completed, or time remaining). The control inputs 68 may enable an operator to adjust the settings of the system 40.

Figure 10:
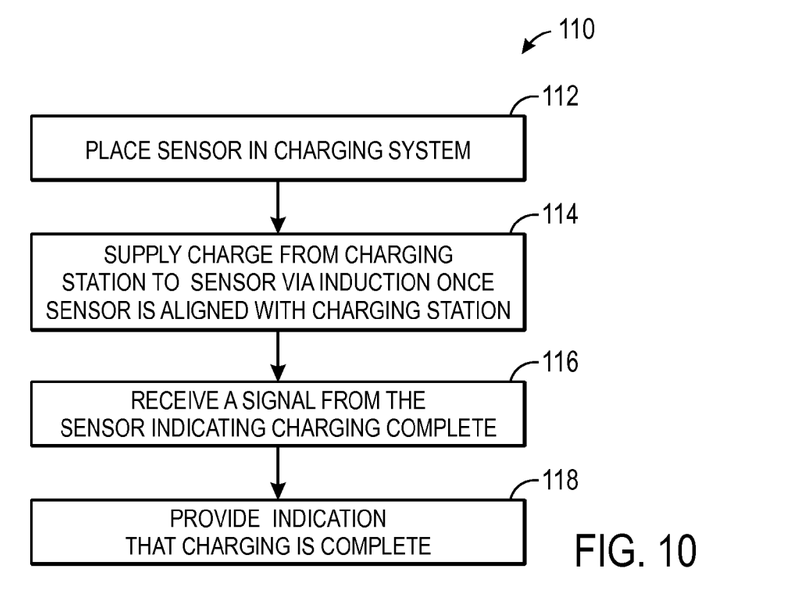
FIG. 10 is a flowchart illustrating a process for charging a sensor, in accordance with an embodiment.

FIG. 10 illustrates a high-level block diagram of an embodiment of a process 110 by which the control circuit 64 may control the system 40 to charge the sensor 10. First, an operator (or automated device) may place the sensor 10 in the charging system (block 112). The sensor 10 will align with the charging station 70 due, at least in part, to the corresponding geometries of the sensor 10 and the charging station 70 as well as the magnets 32 in the sensor 10 and the corresponding magnets 74 in the charging station 70.

The operator (or the device 42 or the sensor 10) may determine whether the sensor 10 is properly aligned with the charging station 70 (block 114). The operator may determine the sensor 10 is properly aligned by visualizing that the sensor 10 is within a lined or marked boundary of the charging station 70. The sensor 10 or the device 42 may be configured to sense or determine whether magnets 32, 74 (or other components of the sensor 10 and charging station 70, such as the induction coils 30, 72) are aligned, in other embodiments. Additionally, in some embodiments, no positive determination of alignment is required, but rather the device 42 is configured to charge whenever the sensor 10 is aligned. In other words, the device 42 may be connected to a power supply 48 such that the induction coil 72 receives a charge and is prepared to supply the charge to any coil 32 that is brought into proximity or alignment.

Once the sensor 10 is aligned with the charging station 70, a charge will be supplied to the sensor 10 via induction (block 114). More particularly, the control circuit 64 may send a charging signal to direct the power from the main power supply 48 to the induction coil 72. The electrical power runs through the induction coil 72 and produces an electromagnetic field which induces an electrical current in the induction coil 30 of the sensor 10. The sensor 10 may use the electrical current to recharge the battery 28. When charging is complete, the control circuit 64 may receive a signal from the sensor 10 indicating that charging is complete (block 116). For example, the sensor 10 may be configured to determine when charging is complete (e.g., via battery meter 84), and the sensor 10 may communicate to the charging station 70 and/or device 42 that the charging is complete (e.g., battery 28 is fully charged). The control circuit 64 of the charging and disinfecting system 42 may also provide an indication (e.g., text, beep, or a light) that charging is complete, thus notifying the operator that the reusable sensor may be used again (block 118). The indication may be a displayed on the display 66. For example, a green light may be displayed on the display 66 when the sensor 10 is fully charged. In some embodiments, the control circuit 64 may terminate the charging signal to prevent the supply of power to the induction coil 72.

The system 40 may also disinfect the sensor 10 simultaneously while charging the sensor 10. As such, a portion of the charging cycle and a portion of the disinfecting cycle may overlap. As discussed above, the disinfecting agent may be supplied via one or more inlets 52 connected to a disinfecting agent supply source 54. The time for disinfecting may be set by an operator through control inputs on the device 42, or may otherwise be controlled or monitored by the operator. Additionally, in certain embodiments, the sensor 10 may communicate the appropriate disinfecting time for the particular sensor 10 to the device 42. When the time for disinfecting is complete, the control circuit 64 of the device 42 may provide an indication (e.g., a text, beep, or a light) that the disinfecting is complete. In yet other embodiments, the device 42 may be equipped with a detector (e.g., a motion detector, weight sensor, or the like) to identify when the sensor 10 has been deposited into the disinfecting agent within the device 42. In such embodiments, the device 42 may further be programmed to disinfect the sensor 10 for a specified period of time, and the device 42 may therefore determine when the disinfecting is complete. In certain embodiments, the control circuit 64 may drain the disinfecting agent from the device 42 upon completion of disinfection, thus allowing the operator to more easily remove the disinfected sensor 10 without having to use tongs or another device to remove the sensor from the disinfecting solution.

In some reusable sensors, it may be desirable to receive a signal or indication when the seal or housing of the sensor is breached. Thus, with reference to FIGS. 11-14, disclosed herein are embodiments of a reusable sensor 120 that may have an indicator, such as a dye 122, disposed (e.g., embedded, integrated, impregnated, etc.) in a housing 124 of the sensor, wherein the dye 122 is configured to exit (e.g., leach, move, seep, etc.) out of the sensor 120 when the sensor housing 124 is damaged. The dye 122 may take any form that, when leached out of the sensor 120, causes a surrounding solution to change color. For example, the dye 122 may be a liquid (e.g., liquid food coloring) or a powder (e.g., colored powder). Such features may be particularly useful in the context of reusable sensors 120 having a rechargeable battery and an encapsulating housing 124 without crevices or openings for battery removal or for wired cable connection. Such reusable sensors 120 may develop holes, punctures, or degradation on external surfaces of the housing 124 due to various factors such as operator manipulation or wear and tear over time. This type of damage may be particularly likely at or on patient-contacting surfaces of the sensor 120. When the reusable sensor 120 develops a puncture, the sensor 120 should not be disinfected (e.g., placed in a disinfecting agent) and reused, but rather, such sensors 120 should be discarded or repaired. For example, soaking damaged sensors 120 in a liquid disinfecting solution may allow the solution to enter into the sensor housing 124 and injure the various electronic components of the sensor 120. When the electronic components of the sensor 120 are damaged, the sensor 120 may no longer be operable or reliable, and the sensor 120 may not be able to provide accurate data, for example. Such a damages sensor 120 should be repaired before use, or discarded.

Figure 11:
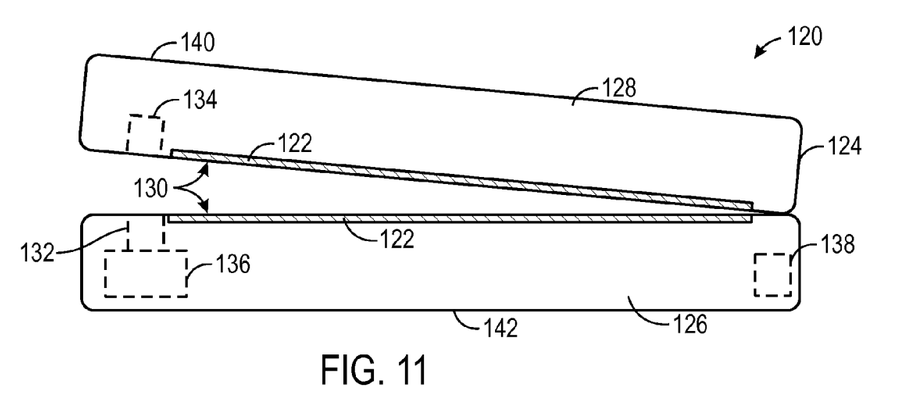
FIG. 11 is a side view of a sensor having a dye within the sensor, in accordance with an embodiment.

Turning to FIG. 11, one embodiment of the pulse oximetry sensor 120 having the dye 122 disposed in the sensor housing 124 is depicted. Although a clip-style pulse oximetry sensor 120 is illustrated, the dye 122 may be utilized with a wide variety of sensors. The clip-style sensor of FIG. 1 includes a bottom portion 126, a top portion 128, and two patient contacting surfaces 130. The sensor 120 may include one or more emitters 132 and one or more detectors 134 connected to circuitry 136. Additionally, in some embodiments, the sensor 120 may be a wireless sensor 120 and may include a wireless transceiver 138. A wireless sensor 120 may not require connection to any cables for transferring data to an external device, such as an external monitor, for example. Thus, a wireless sensor 120 may have an encapsulating housing 124, without any crevices or openings in the housing. As discussed above, the encapsulating housing 124 may facilitate efficient and thorough disinfecting of the wireless sensor 120. Additionally, in some embodiments, the wireless sensor 120 may also include a rechargeable battery (e.g., a battery configured to be charged via the induction system and methods described above).

As illustrated in FIG. 11, the dye 122 may be disposed or embedded within the housing 124 proximate to (e.g., near) one or more of the patient contacting surfaces 130. Such a location may be desirable because the patient contacting surfaces 130 may be more susceptible to wear and tear and degradation. Accordingly, disposing the dye 122 proximate to the patient contacting surfaces 130 may allow an early determination that the housing 124 is broken. In other embodiments, the dye 122 may be disposed proximate other surfaces of the sensor 120, such as proximate to a top surface 140 or a bottom surface 142. Generally, it may be advantageous to dispose the dye 122 proximate to one or more surfaces of the sensor 120 (e.g., between the surface and the electronic components) so that the damage may be identified before the damage (e.g., a puncture) reaches an interior portion of the sensor 120 containing the electronic components of the sensor 120. If the defect is identified before the puncture reaches the electronic components, then the sensor's housing 124 may be repaired and the sensor 120 may be reused. Or, the electronic components of the sensor 120 may be removed from the punctured housing 124 and recycled into a new sensor 120 before being damaged by exposure to air, disinfecting solution, or the like. Generally, the dye 122 may be impregnated into all or a portion of the housing 124 material, or the dye may be compartmentalized and/or contained within a separate pocket or a separate layer formed within the housing 124.

Figure 12:
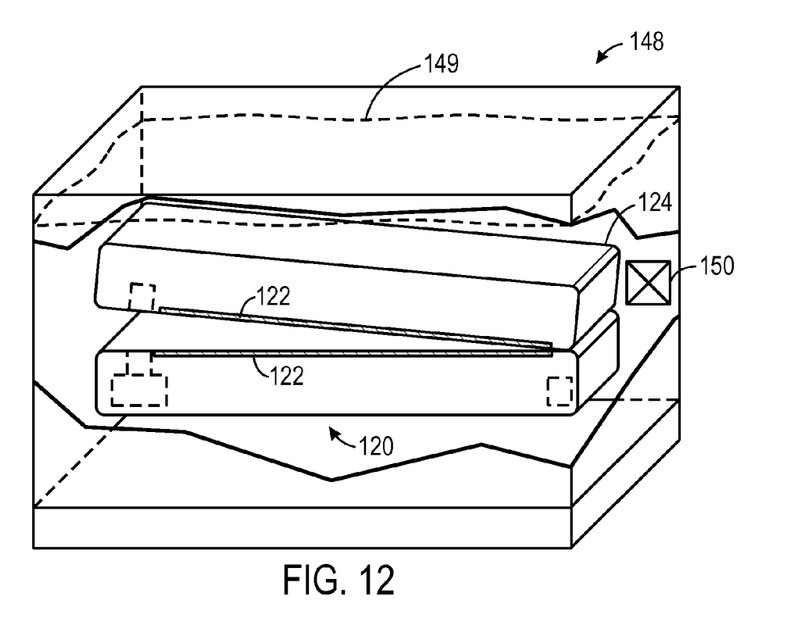
FIG. 12 is a side view of the sensor of FIG. 11 submerged in a solution, in accordance with an embodiment.
Figure 13:
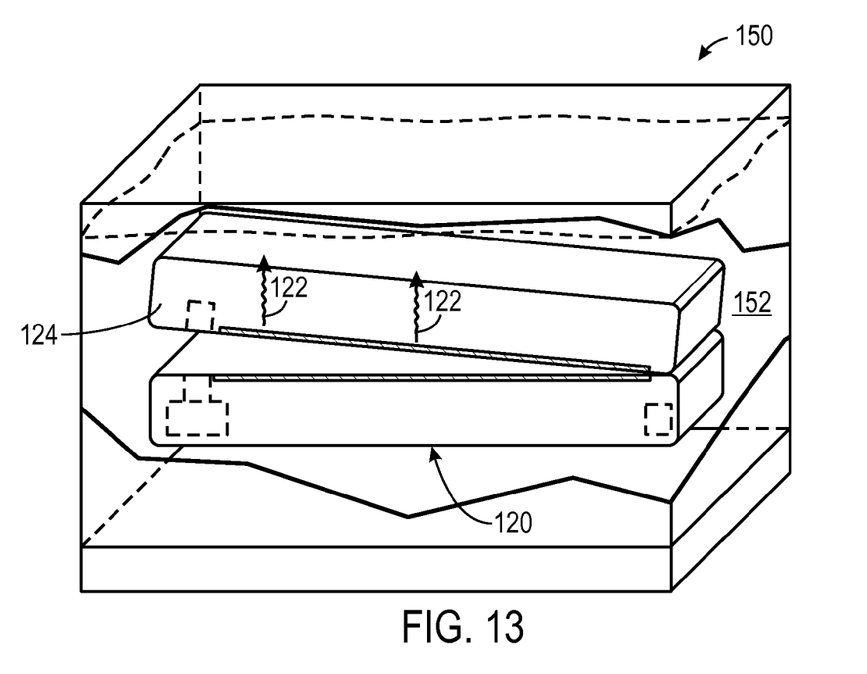
FIG. 13 is a side view of a damaged sensor submerged in the solution, in accordance with an embodiment.

FIG. 12 illustrates the sealed sensor 120 within a disinfecting device 148. As shown, a disinfecting agent 149 (e.g., a disinfecting solution) surrounds the sensor 120. Because the encapsulating housing 124 of the sensor 120 is intact, no dye 122 is present within the disinfecting solution 149. However, FIG. 13 illustrates the sensor 120 with a damaged housing 124. When the housing 124 is punctured, the dye 122 may disperse from the sensor 120 into the disinfecting solution 149. More particularly, as shown, the dye 122 may leach out of the damaged sensor housing 124 into the chamber 152 holding the disinfecting solution 149. In such cases, the disinfecting solution 149 within the chamber 152 may change color or have a change in light absorption or scattering properties due to the presence of the dye 122, for example. The change in color or other properties of the disinfecting solution 149, in turn may signal to the operator that the sensor's housing 124 is damaged (e.g., no longer sealed).

In certain embodiments, the device 148 may be configured to sense or detect the presence of the dye 122 within the disinfecting solution 149. For example, the device 148 may include or may be coupled to a laser, LED, or other narrow band or broadband light source 150 that is configured to detect a change in light intensity or spectrum due to change in scattering or absorption of the disinfecting solution 149. When such a change is detected, the device 148 may provide an indication (e.g., a beep, light, etc.) to the operator, alerting the operator that the sensor 120 is damaged. In cases where the device 148 is configured to charge the sensor 120 (in addition to disinfecting the sensor, such as in the methods described above), the device 148 may be configured not to charge the sensor 120 if it has been determined that the sensor housing 124 is damaged (i.e., if dye 122 is detected in the disinfecting solution 149).

Figure 14:
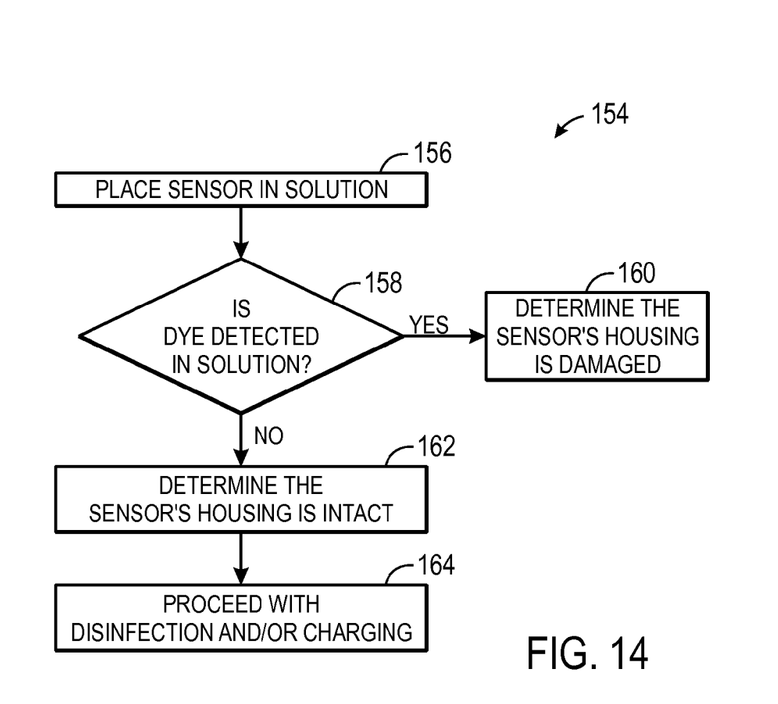
FIG. 14 is a flow chart illustrating a process for evaluating the condition of the sensor, in accordance with an embodiment.

FIG. 14 provides a flowchart of a method 154 for evaluating the condition of the sensor 120. Initially, the sensor 120 may be placed into the solution (block 156). The operator or the device 150 may determine whether the dye 122 is detected in the solution (block 158). If the dye 122 is detected within the solution, then the operator or the device 150 may determine that the sensor's housing 124 is damaged (block 160). If the dye 122 is not detected in the solution, then the operator or the device 150 may determine that the sensor's housing 124 is intact (block 162) and may proceed with disinfecting and/or charging the sensor 120 (block 164).

Although the illustrated embodiments are pulse oximetry monitoring systems, it should be noted that the sensor 120 may be configured to perform any number of measurements on a patient to determine one or more physiological parameters of the patient. That is, while the sensor 120 may determine pulse rates and blood oxygen saturation levels (e.g., $SpO_2$ values) for a patient, the sensor 120 may, additionally or alternatively, be configured to determine a patient's respiration rate, glucose levels, hemoglobin levels, hematocrit levels, tissue hydration, regional saturation, as well as other physiological parameters.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims. Further, individual features of the disclosed embodiments may be combined or exchanged.

What is claimed is:

1. A medical sensor comprising:
   a sensor housing;
   an emitter disposed in the sensor housing, the emitter being configured to direct light through the tissue of a patient;
   a detector disposed in the sensor housing, the detector being configured to detect light from the emitter after the light has passed through the tissue of the patient and to convert the detected light to an electrical signal;
   a rechargeable battery disposed in the sensor housing, the rechargeable battery being adapted to provide power to the emitter and the detector;
   a first induction coil in the sensor housing and electrically coupled to the rechargeable battery, wherein the first induction coil is operable to inductively receive electrical power and is operable to supply charging power to the rechargeable battery;
   at least one magnet disposed in the sensor housing, wherein the magnet is configured to align the first induction coil with a generally horizontal surface to enable the first induction coil to receive electrical power from a second induction coil; and
   a dye disposed in the sensor housing, wherein the dye is configured to exit the sensor housing when the sensor housing is damaged and in the presence of a solution.

2. The sensor of claim 1, comprising a plurality of magnets circumferentially disposed about the first induction coil.

3. The sensor of claim 1, wherein the medical sensor is a clip-style sensor and the sensor housing comprises a top portion and a bottom portion configured to clip to a tissue of a patient, wherein the rechargeable battery and the first induction coil and the at least one magnet are disposed in the bottom portion of the sensor housing.

4. The sensor of claim 3, wherein the bottom portion is heavier than the top portion.

5. The sensor of claim 1, comprising a wireless transceiver disposed in the sensor housing and configured to wirelessly communicate with a patient monitor.

6. The sensor of claim 1, comprising circuitry configured to determine whether the first induction coil is aligned to receive the electrical power.

7. The sensor of claim 6, wherein the circuitry is configured to provide an indication to an external charging device that the first induction coil is aligned.

8. The sensor of claim 1, wherein the sensor housing comprises an external surface and one or more electrical components, and wherein the dye is disposed in the sensor housing between the external surface of the sensor housing and the one or more electrical components.

9. The sensor of claim 1, wherein the dye is disposed proximate a patient contact surface of the sensor housing.

10. The sensor of claim 1, comprising circuitry configured to identify a disinfecting duration for the sensor.

11. A charging and disinfecting system for medical sensors comprising:
    a housing comprising:
        a disinfecting chamber configured to receive and to hold a disinfecting agent; and
        a charging station disposed below the disinfecting chamber, wherein the charging station comprises an induction coil configured to receive electrical power from an electrically connected power supply and at least one magnet disposed proximal to the induction coil;
        wherein the system is configured to detect the presence of a dye within the disinfecting agent and to block delivery of the electrical power from the electrically connected power supply to the induction coil if the dye is detected within the disinfecting agent.

12. The system of claim 11, wherein the charging station comprises a plurality of magnets circumferentially disposed about the induction coil.

13. The system of claim 11, comprising a control circuit configured to determine whether a medical sensor placed within the disinfecting chamber is aligned with the charging station.

14. The system of claim 13, wherein the control circuit is configured to send a charging signal to direct power from the power supply to the induction coil of the charging station for charging the sensor after the control circuit determines the medical sensor is aligned with the charging station.

15. The system of claim 11, comprising a display configured to provide an indication when a medical sensor is aligned with the charging station, or when the medical sensor is fully charged, or both.

16. A rechargeable medical sensor system comprising:
    a medical sensor comprising:
        a sensor housing comprising:
            one or more emitters;
            one or more detectors;
            a rechargeable battery configured to provide power to the one or more emitters and the one or more detectors;
            a first induction coil electrically coupled to the rechargeable battery;
            at least one magnet disposed proximal to the first induction coil;

a dye disposed in the sensor housing, wherein the dye is configured to exit the sensor housing when the sensor housing is damaged and in the presence of a solution and a charging device comprising:

a housing comprising a charging station, wherein the charging station comprises a second induction coil configured to be electrically coupled to an external power supply and at least one magnet disposed proximal to the second induction coil;

wherein the at least one magnet of the charging device is configured to attract the at least one magnet of the medical sensor and to substantially align the first induction coil of the medical sensor with the second induction coil of the charging device and to maintain the first induction coil of the medical sensor within operational proximity of the second induction coil of the charging device to facilitate recharging of the battery.

17. The system of claim 16, wherein the housing comprises a disinfecting chamber configured to hold a disinfecting agent, and the charging station is disposed below the disinfecting chamber of the charging device.

18. The system of claim 16, wherein the medical sensor is configured to wirelessly communicate with a control circuit of the charging device.

19. The system of claim 16, wherein a control circuit of the charging device is configured to determine whether the first induction coil of the medical sensor is aligned with the second induction coil of the charging station and to send a charging signal to direct power from the power supply to the second induction coil after the control circuit determines the first and second induction coils are aligned.

20. The system of claim 16, comprising a display configured to provide an indication when the first induction coil of the medical sensor is aligned with the second induction coil of the charging station, or when the medical sensor is fully charged, or both.

21. The system of claim 16, wherein the sensor housing of the medical sensor is devoid of openings accessing the rechargeable battery.

22. The system of claim 16, wherein the dye is disposed in the sensor housing between an external surface of the sensor housing and an electrical component of the sensor.

* * * * *